United States Patent [19]

Connor

[11] 4,198,511
[45] Apr. 15, 1980

[54] 1,5-DIHYDRO-1,5-DIOXO-N-1H-TETRAZOL-5-YL-4H-[1]BENZOPYRANO[3,4-B]PYRIDINE-3-CARBOXAMIDES AND PROCESS THEREOF

[75] Inventor: David T. Connor, Ann Arbor, Mich.

[73] Assignee: Warner-Lambert Company, Morris Plains, N.J.

[21] Appl. No.: 22,390

[22] Filed: Mar. 21, 1979

[51] Int. Cl.$^2$ ............................................. C07D 491/04
[52] U.S. Cl. ..................................... 546/92; 424/256; 260/343.45
[58] Field of Search ......................................... 546/92

[56] References Cited

U.S. PATENT DOCUMENTS 3,689,497  9/1972  Brown et al. ........................ 546/92

*Primary Examiner*—John D. Randolph
*Attorney, Agent, or Firm*—Stephen Raines; George M. Kaplan; Frank S. Chow

[57] ABSTRACT

The present invention relates to 1,5-dihydro-1,5-dioxo-N-1H-tetrazol-5-yl-4H-[1]benzopyrano[3,4-b]pyridine-3-carboxamides having the following structural formula:

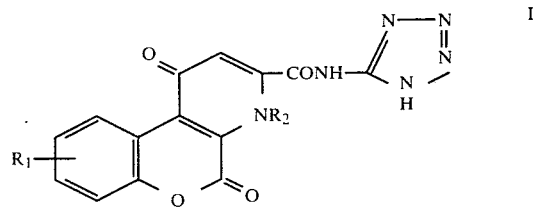

wherein $R_1$ is hydrogen, halogen, hydroxy, lower alkoxy, lower alkyl or nitro and $R_2$ is hydrogen or lower alkyl.

These compounds and their pharmaceutically acceptable salts are useful in the management of allergic manifestations such as bronchial asthma, hay fever and the like.

4 Claims, No Drawings

1,5-DIHYDRO-1,5-DIOXO-N-1H-TETRAZOL-5-YL-4H-[1]BENZOPYRANO[3,4-B]PYRIDINE-3-CARBOXAMIDES AND PROCESS THEREOF

The present invention relates to certain benzopyrano derivatives and more particularly 1,5-dihydro-1,5-dioxo-N-1H-tetrazol-5-yl-4H-[1]benzopyrano[3,4-b]pyridine-3-carboxamides having the following structural formula:

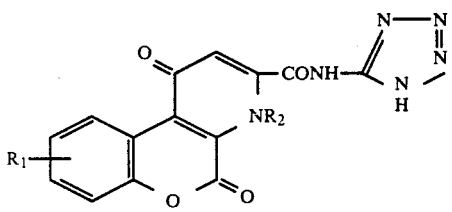

wherein $R_1$ is hydrogen, halogen, hydroxy, lower alkoxy, lower alkyl or nitro and $R_2$ is hydrogen or lower alkyl and the corresponding pharmaceutically acceptable salts thereof.

In the above definitions for $R_1$ and $R_2$, the term "lower alkyl" and the lower alkyl portion of "lower alkoxy" is meant to include both straight and branched chain alkyl radicals having 1 to 6 carbon atoms, for example methyl, ethyl, propyl, isopropyl, n-butyl, and the like. The term "halogen" is meant to embrace all its four members i.e. iodine, bromine, fluorine, and chlorine.

The compounds of this invention, as well as their pharmaceutically acceptable salts, are active in the prevention of allergic reactions in mammals such as mice, rats and guinea pigs. Typically, using rats as the host, and employing the passive cutaneous anaphalaxis (PCA) test, which is described in *Life Sciences*, 7; 465 (1963), *Proc. Soc. Exptl. Biol. Med.*, 81; 585 (1952) and U.S. Pat. No. 4,076,720, the compounds of this invention or their salts were effective in preventing allergic manifestations at a dose level of 5 mg/kg to 100 mg/kg. Typically, the compound 1,5-dihydro-1,5-dioxo-7-methoxy-N-1H-tetrazol-5-yl-4H-[1]benzopyrano[3,4-b]pyridine-3-carboxamide shows a 46% inhibition of the allergic response at an intraperitoneally dose of 5 mg/kg when tested in accordance with the aforedescribed test procedures.

The well known antiallergic compound cromolyn sodium shows 50% inhibition at 2 mg/kg intravenously in the PCA test.

The compounds in this invention including their salts are indicated in the management of mammals suffering from allergic manifestations such as bronchial asthma and hay fever. Generally speaking, a dose of 5 mg/kg to 100 mg/kg orally, parenterally, or by inhalation 1 to 3 times daily is suggested. As with any antiallergy therapy, the above dosage regiment must be titrated to individual needs by methods known to the healing arts.

According to a further feature of the present invention, there are provided pharmaceutical compositions which comprise as active ingredients, at least one of the compounds of this invention or their salts as hereinbefore defined, together with a pharmaceutical carrier. Thus for example, solid compositions for oral administration include compressed tablets, pills, dispensable powders and granules. In such solid compositions, the selective active ingredients are mixed with at least one inert diluent such as calcium carbonate, calcium sulphate, or lactose. These compositions may also comprise, as known to the pharmacist art additional substances other than diluents, such as lubricating agents for example magnesium stearate. The resulting dosage forms such as tablets are prepared by methods known to the pharmacist art.

Liquid compositions for oral administration include for example, solutions, suspensions, syrups and elixirs containing inert diluents commonly used in the preparation of such dosage forms for example, water and simple syrup.

Preparations for parenteral administration include for example, sterile aqueous or non-aqueous solutions or suspensions. Examples of non-aqueous solvents or suspending media are for example, propylglycol, vegetable oils such as olive oil and injectable organic esters such as ethyl oleate.

According to the present invention, Compound I is prepared from $R_1$ - substituted 3-amino coumarin of the formula.

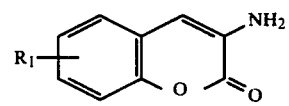

with dimethyl acetylenedicarboxylate of the formula:

This reaction is generally affected at room temperature i.e. between 15° C.-22° C. in a lower molecular weight alcohol such as methanol to obtain a compound of the formula:

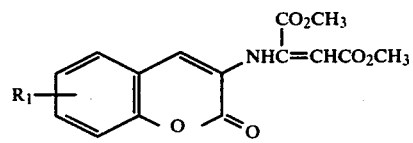

Heating compound IV, in diphenyl ether at elevated temperature such as from 274° C.-285° C. under an inert atmosphere such as under atmosphere of nitrogen results in the production of a compound of the formula:

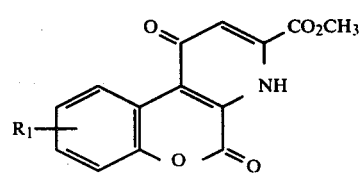

The corresponding acid of the formula:

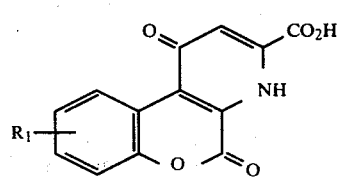

is obtained by acid hydrolysis of Compound V. Finally, one equivalent of Compound VI is treated with at least two equivalents of 1,1'-carbonyldiimidazole of the formula:

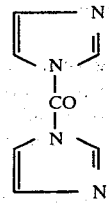

VII to obtain an intermediate of the formula:

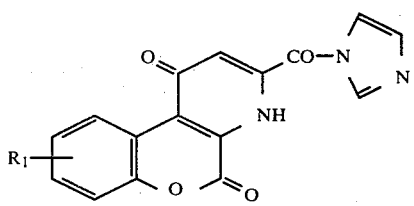

VIII

Compound VIII is generally not isolated but treated directly with at least one equlivalent of 5-aminotetrazole to give those compounds the invention in which $R_2$ is hydrogen i.e. compound X of the formula:

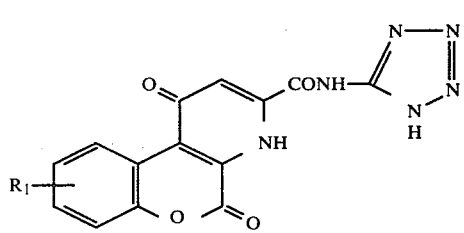

To obtain those compounds of the invention in which $R_2$ is lower alkyl, Compound V is N-alkylated utilizing procedures known in the art such as for example, using dimethyl sulphate.

Generally speaking, the reaction between Compounds VI and VII is affected in a temperature of above 100° C. over a period from about 45 minutes to about 120 minutes in dimethylformamide.

The conversion from VIII to X is also affected at about 100° C. over a period from about 45 minutes to about 180 minutes. Typically, the conversion from VI to VII and from VII to VIII can be accomplished within 60 minutes.

The starting $R_1$ substituted amino coumarins are prepared in accordance with the method of F. W. Lynch, *J. Chem. Soc.*, 101, 1758 (1912). This disclosure, as well as the disclosures in *Life Sciences, Proc. Soc. Exptl. Biol. Med.* and U.S. Pat. No. 4,076,720 referred to above, are incorporated herein by reference.

The $R_1$-substituted aminocoumarins may also be prepared by my disclosure in copending application Ser. No. 22,389 entitled (2-Oxo-2H-1-benzopyran-3-yl) aminooxacetic acids and their derivatives, filed concurrently herewith. This is also incorporated herein by reference.

The pharmaceutically acceptable salts of Compound I are prepared by treating Compound I with an acid such as with a mineral acid, for example, hydrochloric, sulfuric, nitric and so on or an organic acid such as acetic using methods known in the art.

In order to further illustrate the practice in this invention, the following examples in which temperature referred to therein are in degrees centigrade are included:

EXAMPLE 1

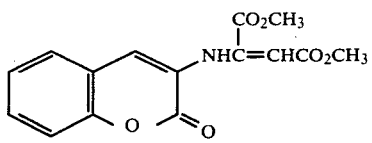

2-Butenedioic acid, 2-[2-oxo-2H-1-benzopyran-3-yl)amino]-,dimethyl ester

A mixture of 3-aminocoumarin (3.22 g, 0.02 mole) and dimethyl acetylenedicarboxylate (4.26 g, 0.03 mole) in methanol (50 ml) is stirred at room temperature for 24 hours. The product is filtered off and washed with methanol. Recrystallization from ethyl acetate gives yellow crystals (5.4 g, 91%), mp 150–151.

Anal. Calcd for $C_{15}H_{13}NO_6$: C, 59.40; H, 4.32; N, 4.62; Found: C, 59.53; H, 4.42; N, 4.61.

EXAMPLE 2

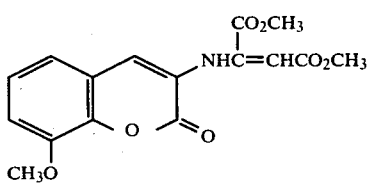

2-Butenedioic acid, 2-[(8-methoxy-2-oxo-2H-1-benzopyran-3-yl)-amino]-, dimethyl ester Prepared by the general method described for example 1 from 8-methoxy-3-aminocoumarin (12.4 g, 0.065 mole). Recrystallization from ethyl acetate gives yellow crystals (17.5 g, 81%), mp 165–167.

Anal. Calcd for $C_{16}H_{15}NO_7$: C, 57.66; H, 4.54; N, 4.20; Found: C, 57.60; H, 4.58; N, 4.01.

EXAMPLE 3

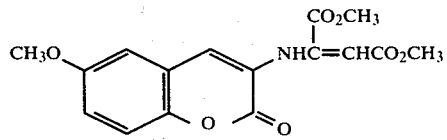

2-Butenedioic acid, 2-[(6-methoxy-2-oxo-2H-1-benzopyran-3-yl)-amino]-, dimethyl ester Prepared by the method described for example 1 from 6-methoxy-3-aminocoumarin (19.1 g, 0.1 mole). Recrystallization from ethyl acetate gives yellow crystals (13.2 g, 39%), mp 152–154.

Anal. Calcd for $C_{16}H_{15}NO_7$: C, 57.66; H, 4.54; N, 4.20; Found: C, 57.32; H, 4.55; N, 3.96.

EXAMPLE 4

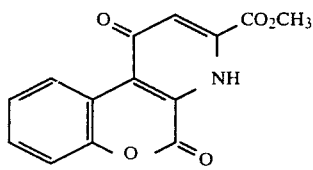

1,5-Dihydro-1,5-dioxo-4H-1-benzopyrano[3,4-b]pyridine-3-carboxylic acid, methyl ester A solution of 2-[(2-oxo-2H-1-benzopyran-3-yl)amino]-2-butenedioic acid, dimethyl ester (3.0 g, 0.0099 mole) in diphenyl ether (50 ml) is heated at 274–285 for 60 minutes under nitrogen. The reaction mixture is cooled and diluted with hexane. The product is filtered off and washed with ethyl acetate. Recrystallization from dimethyl formamide gives white crystals (2.51 g, 93%), mp 225–227.

Anal. Calcd for $C_{14}H_9NO_5$: C, 61.99; H, 3.34; N, 5.16; Found: C, 62.06; H, 3.49; N, 5.07.

EXAMPLE 5

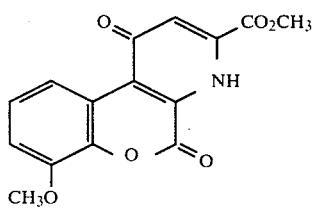

1,5-Dihydro-7-methoxy-1,5-dioxo-4H-1-benzopyrano[3,4-b]pyridine-3-carboxylic acid, methyl ester Prepared by the general method described for example 4 from 2-[(8-methoxy-2-oxo-2H-1-benzopyran-3-yl)amino]-2-butenedioic acid, dimethyl ester (17.0 g, 0.05 mole). The reaction mixture is refluxed for 10 minutes. Recrystallization from dimethyl formamide gives white crystals (8.4 g, 77%), mp 268–272.

Anal. Calcd for $C_{15}H_{11}NO_6$: C, 59.80; H, 3.68; N, 4.65; Found: C, 59.74; H, 3.98; N, 4.72.

EXAMPLE 6

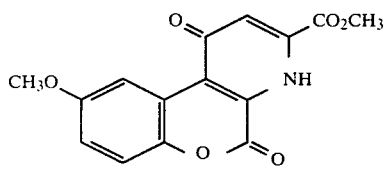

1,5-Dihydro-9-methoxy-1,5-dioxo-4H-1-benzopyrano[3,4-b]pyridine-3-carboxylic acid, methyl ester Prepared by the general method described for example 4 from 2-[(6-methoxy-2-oxo-2H-1-benzopyran-3-yl)amino]-2-butenedioic acid, dimethyl ester (9.9 g, 0.03 mole). The reaction mixture is refluxed for 10 minutes. Recrystallization from dimethyl formamide gives white crystals (6.7 g, 75%), mp 245–250.

Anal. Calcd for $C_{15}H_{11}NO_6$: C, 59.80; H, 3.68; N, 4.65; Found: C, 59.44; H, 3.75; N, 4.56.

EXAMPLE 7

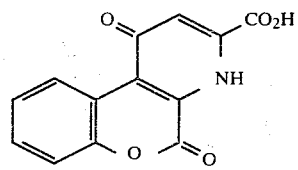

1,5-Dihydro-1,5-dioxo-4H-1-benzopyrano[3,4-b]pyridine-3-carboxylic acid

A suspension of 1,5-dihydro-1,5-dioxo-4H-1-benzopyrano[3,4-b]pyridine-3-carboxylic acid, methyl ester (10.0 g, 0.037 mole) in 5N hydrochloric acid (170 ml) is stirred at 100 for 16 hours under nitrogen. The reaction mixture is cooled. The product is filtered off, washed with water, with acetone and sucked dry. Recrystallization from dimethyl formamide-methanol gives white crystals (6.2 g, 65%), mp 265–268 (dec).

Anal. Calcd for $C_{13}H_7NO_5$: C, 60.71; H, 2.74; N, 5.45; Found: C, 60.30; H, 2.80; N, 5.38.

EXAMPLE 8

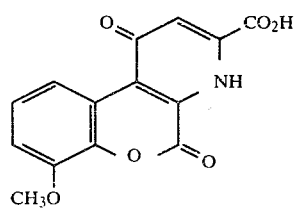

1,5-Dihydro-7-methoxy-1,5-dioxo-4H-1-benzopyrano[3,4-b]pyridine-3-carboxylic acid Prepared by the general method described for example 7 from 1,5-dihydro-7-methoxy-1,5-dioxo-4H-1-benzopyrano[3,4-b]pyridine-3-carboxylic acid, methyl ester (5.4 g, 0.0179 mole). The product is washed with water and with acetone to give white crystals (3.7 g, 72%) mp 290–295 (dec).

Anal. Calcd for $C_{14}H_9NO_6$: C, 58.54; H, 3.16; N, 4.88; Found: C, 58.42; H, 3.35; N, 4.84.

EXAMPLE 9

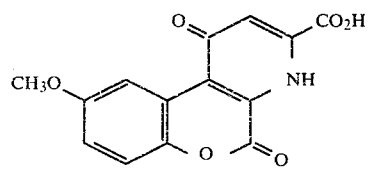

1,5-Dihydro-9-methoxy-1,5-dioxo-4H-1-benzopyrano[3,4-b]pyridine-3-carboxylic acid Prepared by the general method described for example 7 from 1,5-dihydro-9-methoxy-1,5-dioxo-4H-1-benzopyrano[3,4-b]pyridine-3-carboxylic acid, methyl ester (5.0 g, 0.0166 mole). The reaction mixture is stirred 3 days at 100. The product is washed with water and with acetone to give white crystals (4.2 g, 80%), mp 265–270.

Anal. Calcd for $C_{14}H_9NO_6 \cdot \frac{1}{4}H_2O$: C, 57.63; H, 3.26; N, 4.80; Found: C, 57.89; H, 3.15; N, 4.80.

EXAMPLE 10

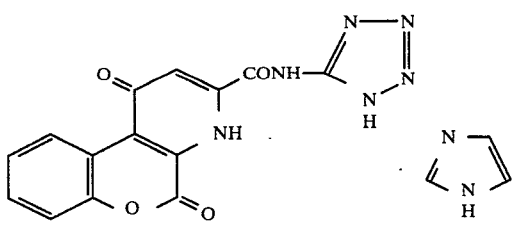

1,5-Dihydro-1,5-dioxo-N-1H-tetrazol-5-yl-4H-[1]benzopyrano-[3,4-b]pyridine-3-carboxamide.

A mixture of 1,5-dihydro-1,5-dioxo-4H-1-benzopyrano[3,4-b]pyridine-3-carboxylic acid (2.57 g, 0.01 mole) and 1,1'-carbonyldiimidazole (3.24 g, 0.02 mole) in dimethylformamide (50 ml) is heated at 100 for 60 minutes under nitrogen. The reaction mixture is cooled. 5-aminotetrazole monohydrate (1.03 g, 0.01 mole) is added and the resulting mixture is heated at 100 for 60 minutes, cooled and filtered. The product is recrystallized from dimethylformamide to give white crystals (1.51 g, 39%) mp 265–270. The product crystallizes as a 1:1 salt or complex with 1H-imidazole.

Anal. Calcd for $C_{17}H_{12}N_8O_4 \cdot \frac{1}{2}H_2O$: C, 50.87; H, 3.24; N, 27.93; Found: C, 50.95; H, 3.28; N, 27.88.

The above compound was tested in accordance with the PCA test. At 5 mg/kg 12% inhibition was found.

EXAMPLE 11

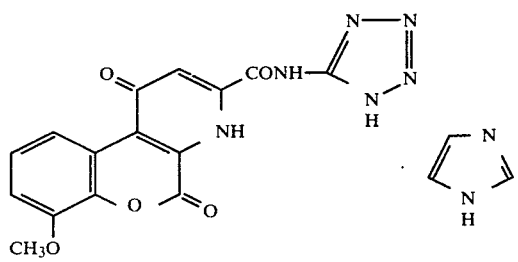

1,5-Dihydro-1,5-dioxo-7-methoxy-N-1H-tetrazol-5-yl-4H-[1]benzopyrano[3,4-b]pyridine-3-carboxamide Prepared by the general method described for example 10 from 1,5-dihydro-1,5-dioxo-7-methoxy-4H-1-benzopyrano[3,4-b]pyridine-3-carboxylic acid (2.87 g, 0.01 mole). The product is washed with dimethylformamide to give white crystals (3.01 g, 70%), mp 248–252 (dec).

Anal. Calcd for $C_{18}H_{14}N_8O_5 \cdot \frac{1}{2}H_2O$: C, 50.12; H, 3.48; N, 25.98; Found: C, 49.96; H, 3.50; N, 25.79.

The above compound was tested in accordance with the PCA test at 5 mg/kg and 46% inhibition was found.

EXAMPLE 12

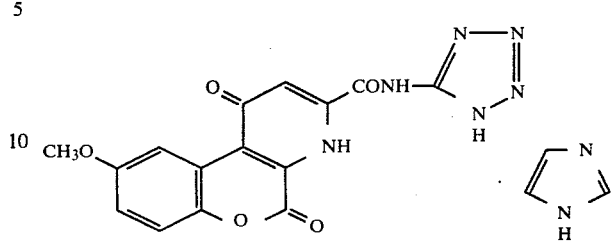

1,5-Dihydro-1,5-dioxo-9-methoxy-N-1H-tetrazol-5-yl-4H-[1]benzopyrano[3,4-b]pyridine-3-carboxamide Prepared by the general method described for example 10 from 1,5-dihydro-1,5-dioxo-9-methoxy-4H-1-benzopyrano[3,4-b]pyridine-3-carboxylic acid (2.87 g, 0.01 mole). The product is washed with dimethylformamide to give pale yellow crystals (3.26 g, 76%), mp 245–250 (dec). The product crystallizes as a 1:1 salt or complex with 1H-imidazole.

Anal. Calcd for $C_{18}H_{14}N_8O_5 \cdot \frac{1}{2}H_2O$: C, 50.12; H, 3.48; N, 25.98; Found: C, 50.17; H, 3.50; N, 25.86.

The above compound was tested in accordance with the PCA test and at 5 mg/kg 24% inhibition was found.

We claim:
1. A compound of the formula:

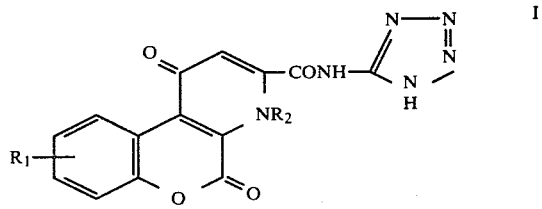

wherein $R_1$ is hydrogen, halogen, hydroxy, lower alkoxy, lower alkyl or nitro and $R_2$ is hydrogen or lower alkyl and the corresponding pharmaceutically acceptable salts thereof.

2. A compound according to claim 1 which is 1,5-Dihydro-1,5-dioxo-N-1H-tetrazol-5-yl-4H-[1]benzopyrano-[3,4-b]pyridine-3-carboxamide.

3. A compound according to claim 1 which is 1,5-Dihydro-1,5-dioxo-7-methoxy-N-1H-tetrazol-5yl-4H[1]benzopyrano[3,4-b]pyridine-3-carboxamide.

4. A compound according to claim 1 which is 1,5-Dihydro-1,5-dioxo-9-methoxy-N-1H-tetrazol-5-yl-4H-[1]benzopyrano[3,4-b]pyridine-3-carboxamide.

* * * * *